United States Patent [19]
Heneveld

[11] Patent Number: 5,415,187
[45] Date of Patent: May 16, 1995

[54] COMBINATION TOOTHBRUSH, TOOTHPASTE DISPENSER AND DENTAL FILAMENT DISPENSER

[76] Inventor: William R. Heneveld, 431 Adaway Dr., Grand Rapids, Mich. 49546

[21] Appl. No.: 970,765

[22] Filed: Nov. 3, 1992

[51] Int. Cl.⁶ .................................. A61C 15/00
[52] U.S. Cl. ............................ 132/325; 132/324
[58] Field of Search .......... 132/323, 324, 321, 325, 132/309; 206/368, 63.5; D28/64

[56] References Cited

U.S. PATENT DOCUMENTS

| | | | |
|---|---|---|---|
| 1,210,207 | 12/1916 | Roach | 132/324 |
| 3,913,597 | 10/1975 | Day | 132/324 |
| 4,050,648 | 9/1977 | Tisma | 132/321 |
| 4,141,519 | 2/1979 | Tarrson et al. | 132/321 |
| 4,934,389 | 6/1990 | Pettiford | 132/325 |
| 4,957,125 | 9/1990 | Yaneza | 132/309 |

*Primary Examiner*—John G. Weiss
*Attorney, Agent, or Firm*—Price, Heneveld, Cooper, DeWitt & Litton

[57] ABSTRACT

Dental filament dispenser is a unique plastic molded unit formed by a housing, a retainer means, and a cover. A filament cut-off element is mounted on the cover and provides a unique way for facilitating the easy grasping of the filament and also completely concealing the filament inside the housing when the cover is closed thereby covering the end of the filament to be grasped. The dental filament dispenser is formed of either one piece or two pieces. The one piece includes the housing, retainer means, and cover molded in one piece. The two pieces include the housing separately molded and the divider member and cover molded in one piece.

6 Claims, 4 Drawing Sheets

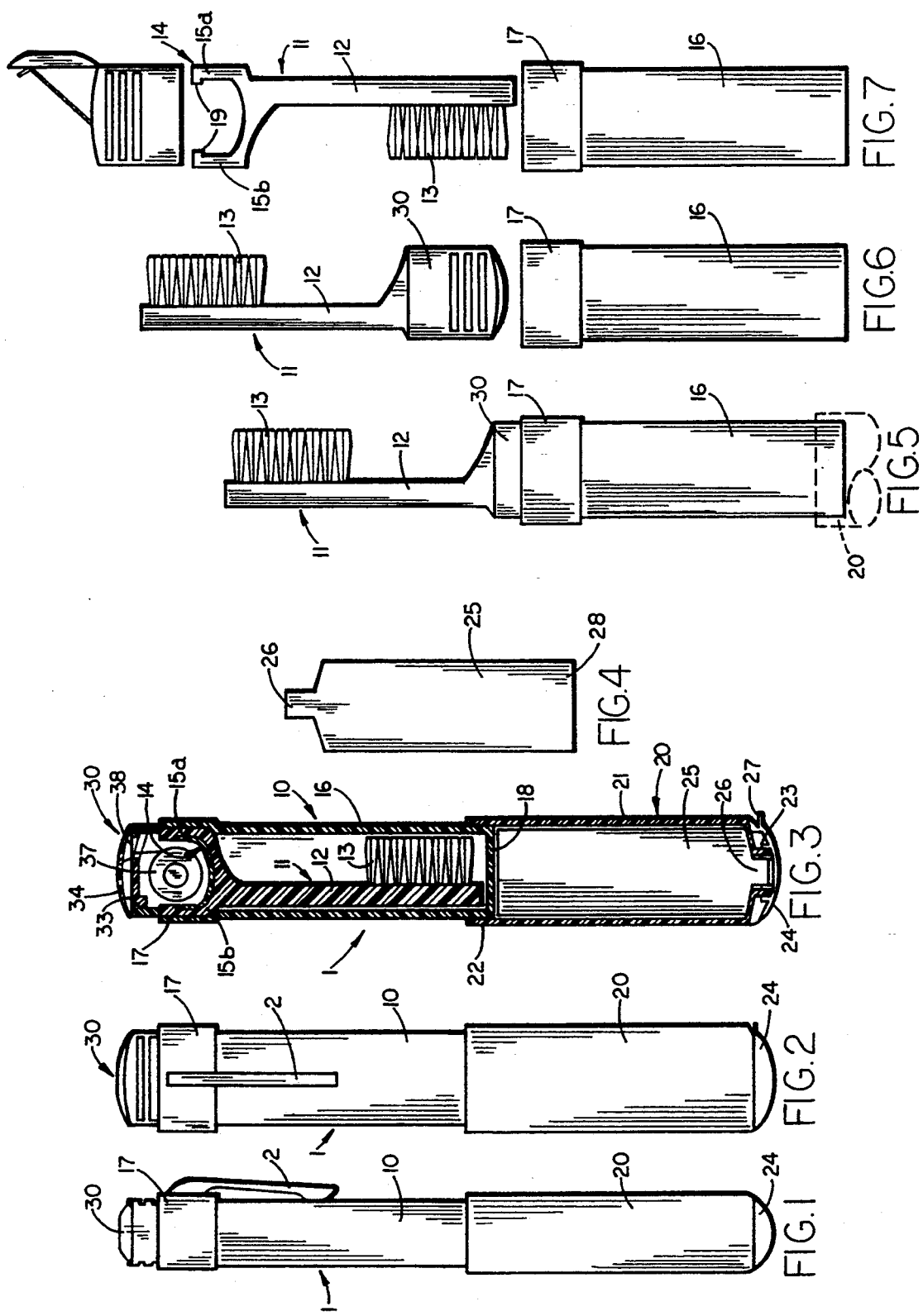

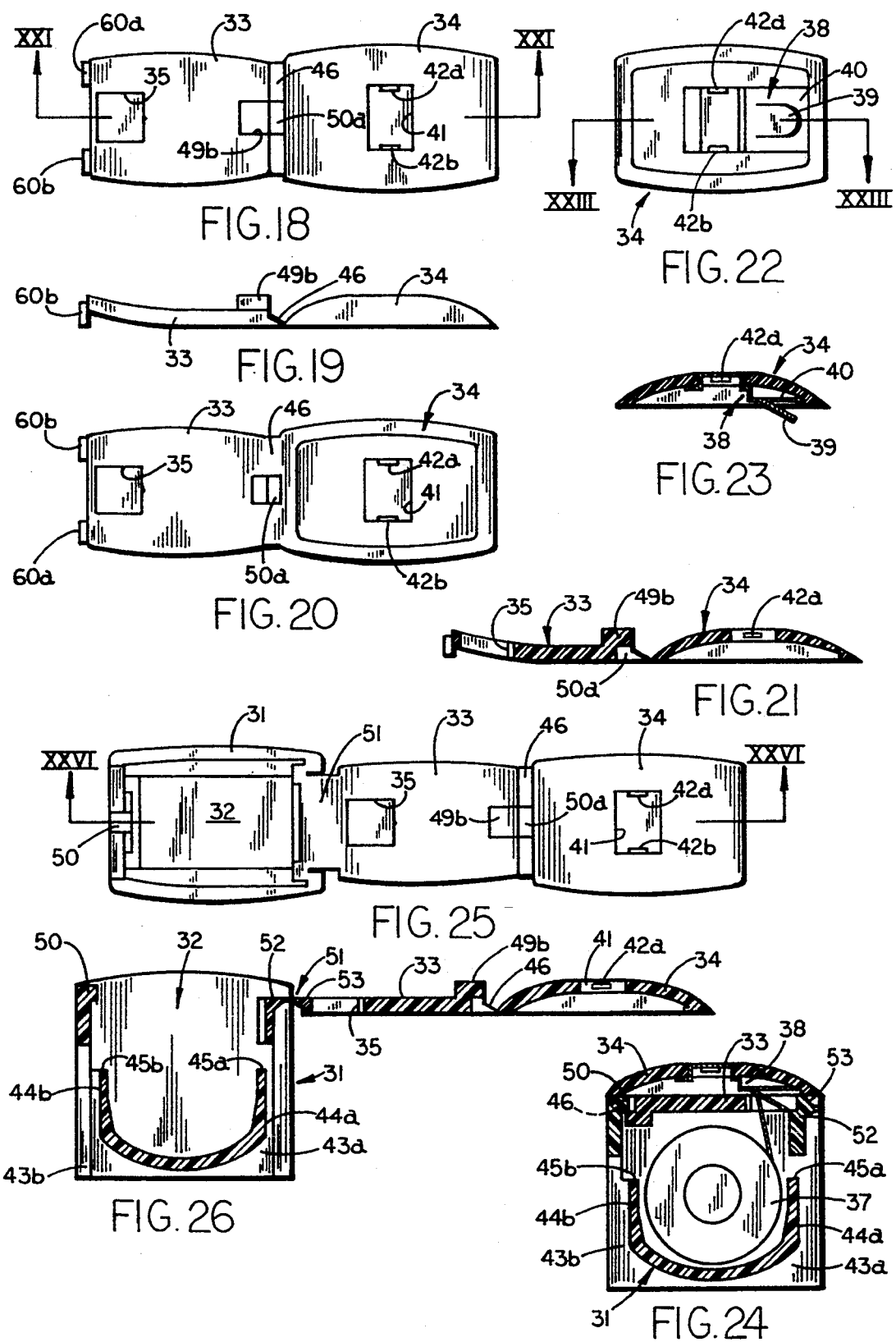

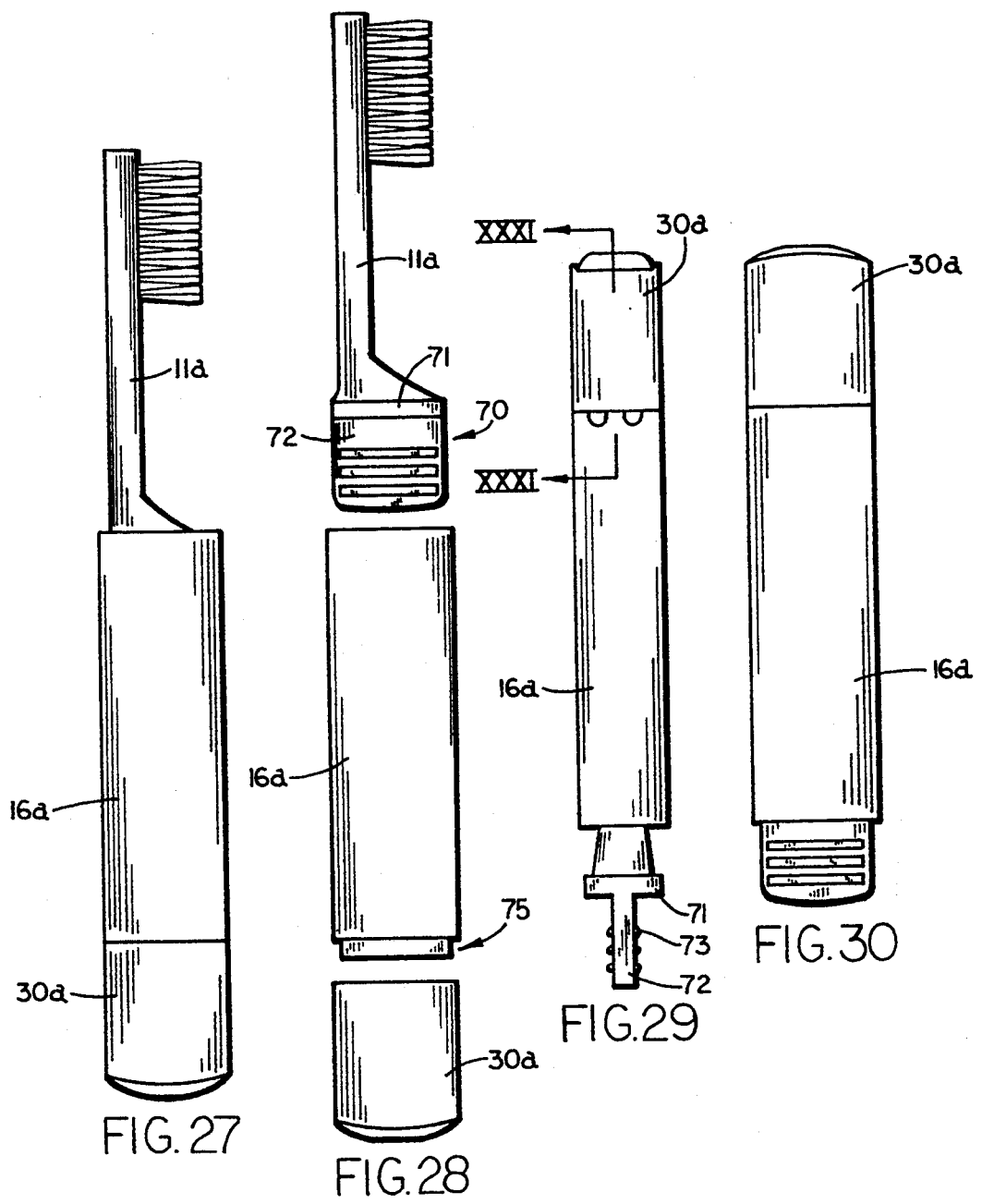

COMBINATION TOOTHBRUSH, TOOTHPASTE DISPENSER AND DENTAL FILAMENT DISPENSER

FIELD OF INVENTION

This invention relates to a personal oral hygiene device which incorporates a toothpaste dispenser and/or a dental filament dispenser into a toothbrush. It also relates to a unique dental filament dispenser that is self-contained and can be sold separate and apart from a toothbrush.

BACKGROUND OF INVENTION

Many different combinations of toothbrushes, toothpaste dispensers, and dental filament dispensers have been designed but all of these devices are very complicated and expensive to manufacture. For example, reference is made to the Boulicault U.S. Pat. Nos. 2,468,732 and 2,468,733 both of which are combination toothbrush, dentifrice and dental filament dispensers, the dentifrice being in the form of a solid stick. In both of these devices, the construction is expensive. Further, the dental filament dispenser construction makes it difficult to grasp the end of the filament without completely dismantling the filament housing from the unit or leaving the end of the filament in the open at all times. It also is almost impossible for the dental filament dispensers to be carried in a pocket or container such as a toiletries kit or a lady's purse. In addition, the filament dispensers have a cut-off element on the outside of the unit, thus leaving the possibility of the element catching on fabric of clothing or on the inside of a container in which the unit is carried.

The prior art units known by me also have no way of completely removing the dental filament dispenser and using it as a self-contained unit that can stand alone as a dispenser and be carried by the user or in the alternative, connected to the toothbrush.

The prior art Units also are made of a number of expensive parts that have to be separately manufactured and assembled which contributes to the overall high cost of the unit.

SUMMARY OF THE INVENTION

The present invention is designed to eliminate the problems and disadvantages of prior art teeth cleaning units such as disclosed in the Boulicault U.S. Pat. Nos. 2,468,732 and 2,468,733. It is made of a minimum number of molded parts that are easily assembled. In accordance with one aspect of my invention, I provide a combination toothbrush, toothpaste dispenser, and dental filament dispenser in which the toothbrush can be carried in a tubular cover for protecting the toothbrush from collecting dirt or germs and also supports a dental filament dispenser that is removable from the toothbrush and usable as a self-contained dental filament dispenser separate and apart from the toothbrush.

In such embodiment, the combination also provides an arrangement whereby a toothpaste dispenser is combined with the toothbrush and/or the dental filament dispenser, the toothbrush and the dental filament dispenser providing a means for ejecting toothpaste from the toothpaste dispenser.

In another embodiment in which the toothpaste dispenser is not used, the dental filament dispenser is uniquely attached to the tubular cover and is detachable therefrom.

In the toothpaste embodiment, the above is accomplished by providing a toothbrush having a stem on one end, the other end of the stem having means for removably supporting a dental filament dispenser that is a self-contained unit easily mountable on one end of the stem opposite the end of the brush. The dental filament dispenser includes a housing formed of a molded body having an upper and lower section. The lower section is configurated to be received in the support means at the end of the stem of the toothbrush and includes a compartment for containing a spool of dental filament.

In both embodiments, the dental filament housing has an opening at its very top for receiving a spool of filament and dispensing the same. The filament is mounted in the housing by a retainer member and a cover is provided to close the housing. The retainer member is preferably a divider member received within the body of the housing closing off access to the spool of filament except for an opening through which the dental filament extends. The cover includes a filament cut-off element that not only cuts the filament but also holds it in position thereby providing a sufficient length of the end of the filament for the operator to grab. However, when the cover is closed, the filament is completely concealed within the housing and thus is protected from dirt and germs. Further, the cut-off element on the housing is unexposed when the cover is closed.

In accordance with my invention, the housing, divider member and cover can be molded in one piece or any two elements can be molded together with the other element being separate and apart until assembled.

The toothpaste dispenser adapted to be assembled with the combination toothbrush and dental filament dispenser includes a tubular housing having an open end in which the tubular cover for the toothbrush slideably fits and can be pushed along substantially the entire length. A pouch of toothpaste is located within the tubular housing. When the tubular cover for the toothbrush is pushed into the tubular housing against the pouch, toothpaste within the pouch is dispensed out of a small opening located at the other end of the tubular housing for the toothpaste.

DESCRIPTION OF THE DRAWINGS

FIG. 1 is a side-elevational view of a combination toothbrush, toothpaste dispenser, and dental filament dispenser in accordance with my invention;

FIG. 2 is a side-elevational view of the combination toothbrush, toothpaste dispenser, and dental filament dispenser of FIG. 1 rotated 90° with respect to the combination as disclosed in FIG. 1;

FIG. 3 is a cross-sectional view of the combination as disclosed in FIGS. 1 and 2;

FIG. 4 is a side-elevational view of a pouch containing toothpaste, such pouch also being shown in the lower half of FIG. 3;

FIG. 5 is a side-elevational view of a combination toothbrush and dental filament dispenser with the toothbrush in position for use in brushing teeth;

FIG. 6 is an exploded view of the combination disclosed in FIG. 5 showing separately the cover for the toothbrush and the brush with dental filament dispenser attached thereto;

FIG. 7 is a side-elevational exploded view of the three components of the combination toothbrush and dental filament dispenser of FIG. 6;

FIG. 18 is a plan view of the cover and divider member molded in one piece;

FIG. 19 is a side-elevational view of the cover and divider member of FIG. 18;

FIG. 20 is another plan view of the opposite side of the cover and divider member of FIGS. 18 and 19;

FIG. 21 is a cross-sectional view of the cover and divider member taken along the plane XXI—XXI of FIG. 18;

FIG. 22 is a plan view of the inside surface of the cover with the filament cutter installed;

FIG. 23 is a cross-sectional view of the cover taken along the plane XXIII—XXIII of FIG. 22;

FIG. 24 is a cross-sectional view of another embodiment of my invention in which the cover, the divider member, and the housing are formed by one molded piece;

FIG. 25 is a plan view of the three parts of the embodiment of FIG. 24, i.e., the housing, the divider member, and cover;

FIG. 26 is a cross-sectional view taken along the plane XVI—XVI of FIG. 25;

FIG. 27 is a side-elevational view of another embodiment of my invention which includes a combination toothbrush and dental filament dispenser with the toothbrush in position for use in brushing teeth;

FIG. 28 is an exploded view of the combination disclosed in FIG. 27 showing separately the toothbrush, the tubular cover for the toothbrush, and the dental filament dispenser;

FIG. 29 is a side-elevational view of the toothbrush and dental filament dispenser of FIGS. 27 and 28 turned upside down from the position of FIGS. 27 and 28 and rotated 90° with the toothbrush partially inserted in the tubular cover;

FIG. 30 is another side-elevational view of the toothbrush and dental filament dispenser of FIG. 29 rotated 90° and completely assembled for carrying or storing;

FIG. 31 is a cross-sectional view taken along the plane XXXI—XXXI of FIG. 29 showing the unique attachment means of the dental filament dispenser to the tubular cover;

FIG. 32 is an exploded partial view of the means shown in FIG. 31; and

FIG. 33 is an exploded view of an alternative means of attaching the dental filament dispenser to the tubular cover.

Figure 8:
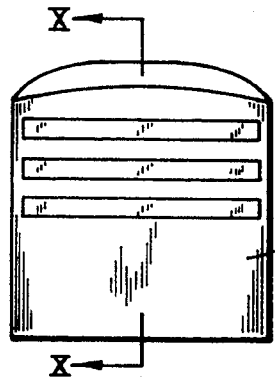
FIG. 8 is a side-elevational view of the dental filament dispenser.

Referring to the drawings, FIG. 1 discloses the overall combination of the toothbrush subassembly 10, the toothpaste dispenser 20, and the dental filament dispenser 30 all interrelated to form one unit that can be carried in the pocket of a person by means of the clip 2 or carried in a container such as a woman's purse, attache case or hygiene type of kits. The various components, including the toothpaste dispenser and the dental filament dispenser 30, can be separated one from the other. For example, the toothbrush subassembly 10 and dental filament dispenser 30 can be utilized as a separate unit by simply removing the toothpaste dispenser 20 therefrom. Further, the dental filament dispenser 30 is a self-contained unit which can be removed from the toothbrush subassembly 10 and utilized as a stand alone dispenser that can be carried in a pocket or a container such as a woman's purse, attache case or toiletries kit.

Figure 14:
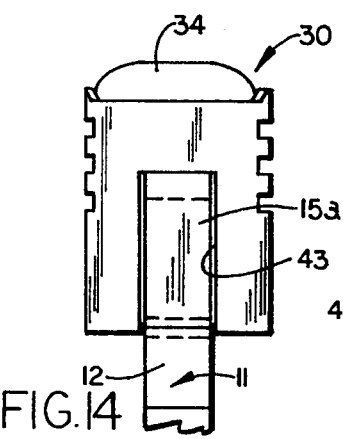
FIG. 14 is a side-elevational view of the end of the toothbrush supporting the dental filament dispenser of this invention.
Figure 16:
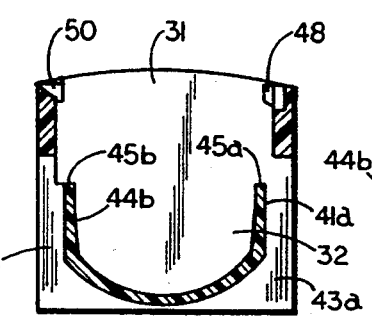
FIG. 16 is a cross-sectional, elevational view of the housing taken along the plane XVI—XVI of FIG. 13.

The toothbrush subassembly is best illustrated in FIGS. 3 and 7 of the drawings wherein is disclosed the toothbrush 11 having a plastic stem 12 at one end of which is the brush 13 and at the other end a support 14 for the dental filament dispenser 30. When the toothbrush is to be stored, it is contained within the plastic tube or cover 16 which is closed at the end 18 and open at the end 17, the open end 17 having an increased diameter matching the curvature and dimension of the support 14 whereby the support 14 with the dental filament dispenser 30 attached can be inserted into the open end 17 for supporting the toothbrush 11 when it is to be used for brushing teeth. The end 14 for supporting the dental filament dispenser includes two legs 15a and 15b (FIGS. 7 and 14) which fit into grooves or channels on opposite sides of the dental filament dispenser 30. These legs 15a and 15b are somewhat resilient so that the detents 19 on each end of the legs 15 (FIG. 7) can be forced over surfaces of grooves formed in the housing of the dental filament dispenser (FIG. 3) and snapped into support position, all of which will be described in greater detail hereinafter.

The toothpaste dispenser 20 includes a plastic tube 20 having an inner diameter identical to the outer diameter of the cover or tube 16 for the toothbrush subassembly. Thus, the tube 16 is firmly held in the open end 22 of the tube 21 and can be slideably pushed into the tube 21. A paste pouch 25 is located or contained within the tube 21. It is constructed of a very thin plastic material such as polyethylene which is easily crushable along the longitudinal axis of the pouch. The pouch 25 is closed at the end 28 and has a reduced diameter neck portion 26 that fits into the neck 23 formed in the other end of the tube 21 opposite the end 22. The neck 26 of the pouch 25 can be snipped with a sharp instrument such as a knife or scissors which then permits the toothpaste within the pouch 25 to be dispensed out of the neck 26. The neck 23 of the tube 21 is covered by a cap 24 molded integrally with tube 21 and which includes a tab 27 for pulling the cap off from the neck 23 to permit the toothpaste within the pouch 25 to be dispensed out of the neck 23. This is accomplished by pushing downwardly, as viewed in FIG. 3, on the tube 16 of the toothbrush subassembly 10 which displaces a portion of the pouch 25 and the toothpaste therein causing it to be dispensed out of the necks 23 and 26.

Figure 17:
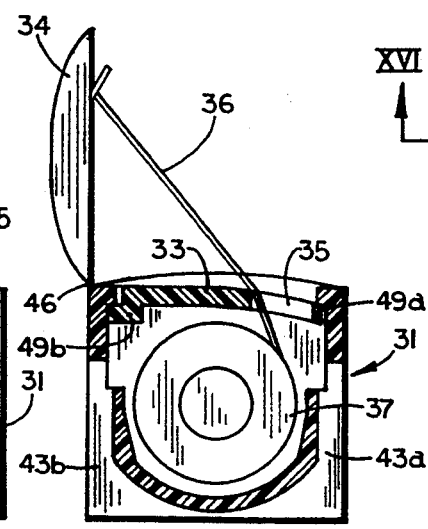
FIG. 17 is a cross-sectional view of the dental filament dispenser assembled and with a spool of filament in place illustrating the accessibility of the end of the filament.

Having described the toothbrush subassembly 10 and the toothpaste dispenser 20, reference is now made to FIGS. 8-23 which discloses the details of the dental filament dispenser 30 which includes the plastic housing 31 molded to provide an opening in the top thereof leading to a chamber 32 in which a spool 37 of dental filament is located (FIGS. 17). The chamber 32 is covered by a divider member 33 and a cover 34. The divider member has an opening 35 (FIG. 17) through which the filament 36 of the filament spool 37 extends. A filament cut-off element 38 is mounted in the cover 34 as disclosed in FIG. 23. It is a metal element having a finger 39 punched out of the section 40 so that when the filament is pulled between the cutout 39 and the section 40 it is cut but, after being cut, is held in place between the cutout portion 39 and the section 40 so as to provide a readily available end to be grasped by the user. The cut-off element 38 is configured to be received within the opening 41 of the cover 34 and held in place by the tabs 42a and 42b (FIGS. 18, 21, 22 and 23).

Figure 9:
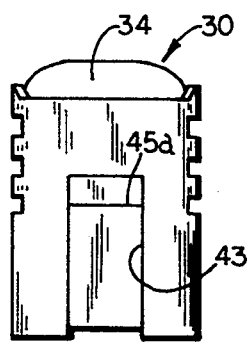
FIG. 9 is another side-elevational view of the dental filament dispenser of FIG. 8 turned 90°.
Figure 10:
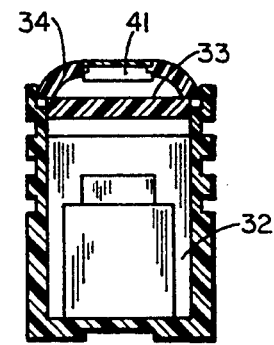
FIG. 10 is a side-elevational, cross-sectional view taken along the plane X—X of FIG. 8.
Figure 12:
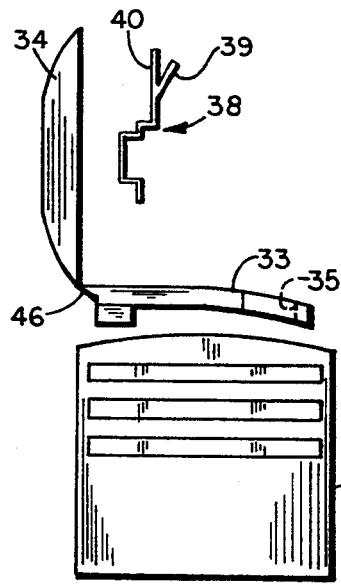
FIG. 12 is an exploded view of the components of one embodiment of my dental filament dispenser.
Figure 15:
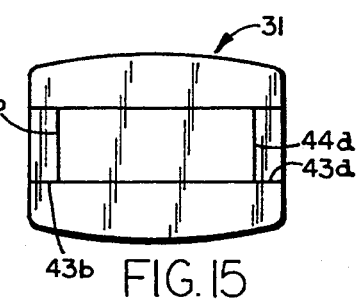
FIG. 15 is a bottom view of the housing.

The narrow sides of the housing 31, as viewed in FIGS. 9 and 15, include the grooves, recesses or channels 43 on opposite sides thereof. Channels 43 are dimensioned to receive the fingers 15a and 15b of the toothbrush subassembly 10 when the dental filament dispenser 30 is attached to the support end 14 of the toothbrush subassembly. When being attached, the inner ends of the fingers 15a and 15b ride along the outer wall 44a and 44b until the protruding ends, that is, the shoulders 19 snap over the edges 45a and 45b of the walls 44a and 44b. Thus, as disclosed in FIG. 3, the dental filament dispenser is supported and held firmly by the fingers 15a and 15b while at the same time providing a cylindrical surface which fits into the enlarged end 17 of the tube 16 when the toothbrush is to be used as illustrated by the exploded view of FIG. 6 and the assembled view of FIG. 5.

Figure 13:
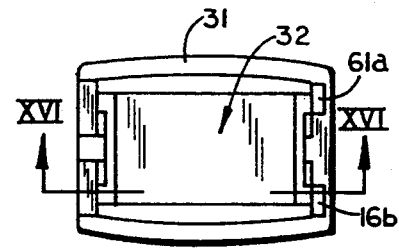
FIG. 13 is a top plan view of the housing for the dental filament dispenser of FIGS. 8-12.
Figure 11:
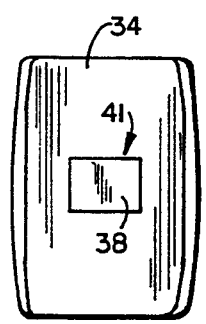
FIG. 11 is a top plan view of the dental filament dispenser of FIGS. 8, 9, and 10.

Referring to FIGS. 12-21, it will be noted that the divider member 33 and cover 34 are constructed of one molded piece by connecting them together by a living hinge 46. The divider member 33 is mounted within the housing 31, as disclosed in FIG. 17, by means of the tabs 60a and 60b (FIG. 18), protrusion 48, and protrusion 50. One end 49a of the divider member 33 is held in by protrusion 48 and prevented from sliding downwardly by tabs 60a and 60b (FIG. 18) which fit in indents 61a and 61b (FIG. 13). End 49b is prevented from sliding downwardly by the angled portion which rests on the housing sidewall. Living hinge 46 and divider member 33 include an opening 50a for receiving the protrusion 50 which prevents the divider member from moving upwardly.

The housing 31 and the divider member 33 and cover 34 are all constructed of a plastic material such as polypropylene which has a sufficient flexibility or resiliency to permit the divider member 33 to be snapped into place by first inserting the end 49a under the protrusion 48 and then snapping end 49b under protrusion 50. Such material has sufficient rigidity for holding the divider member 33 and the attached cover 34 in place.

FIGS. 24, 25, and 26 disclose a modification in which the housing 31, the divider member 33, and the cover 34 are one piece molded integrally with each other, the cover 34 and divider member 33 are attached by the living hinge 46 as in the previous embodiment and the divider member 33 are attached to the housing 31 by the living hinge 51. The presence of the connection 51 requires a slight modification of the housing 31 to accommodate the connection 51. Thus, the end of the housing wherein in FIG. 13, the protrusion 48 and indents 61a and 62b are located, a ledge 52 is provided in lieu thereof. Thus, when the divider member 33 is pivoted into position as disclosed in FIG. 24, the portion 53 of the connection 51 is folded over the ledge 52 which supports the divider member 33 at the one end. The other end is sufficiently supported by the angled portion of the housing side wall and contained by protrusion 50.

FIGS. 27-33 illustrate an alternative means to accomplish a combination toothbrush and dental floss dispenser without the toothpaste dispenser. Shown are modified versions of the toothbrush 11a, toothbrush tubular cover 16a, and dental filament dispenser 30a.

The structure of the modification disclosed in FIGS. 27-33 is very similar to that previously described. The difference is that the dental filament dispenser 30a is attached to the tubular cover 16a rather than the end of the toothbrush 11a which includes an end 70 formed of an element 71 from which the flat extreme end 72 extends. Element 71 is of the same shape and size as the opening in the tubular cover 16a so that it supports the brush 11a in either positions of FIGS. 27 and 30. End 72 includes knurls 73 which facilitate insertion and removal of the brush 11a from the tubular cover.

As disclosed in FIGS. 31 and 32, the end 75 of tubular cover 16a has a reduced dimension and dental filament dispenser 30a includes a recess 76 of substantially the same shape and size as end 75 so as to receive the end 75. The extreme end of the flange 77 forming the recess 76 includes a bead 78 which is received in the dimple 79 located at the juncture between the reduced end 75 and the remainder of the tubular cover 16a. The bead 78 fitting in the dimple 79 assists in holding the filament dispenser on the tubular cover.

FIG. 33 discloses another means for assisting in holding filament dispenser on the tubular cover 16a. It includes the flanges 80 on the wall 81 of the tubular cover 30b and the openings 82 on the reduced end 75 for receiving the flanges 80. Both flanges 80 are shaped to provide a camming surface 83 each of which engage a camming surface 84 so that the flanges 80 can be snapped into the openings 82 for holding the filament dispenser securely on the tubular cover 16b.

OPERATION

The operation of my devices should be evident from the above description. Basically, the unit 1 of FIGS. 1-7 includes all three components capable of being arranged to be used as a toothbrush by simply removing the toothbrush 11 from the tube or cover 16 and turning it upside down in the position as shown in FIG. 6 and then forcing the end of the toothbrush opposite the brush 13 on which the dental filament dispenser is mounted into the end 17 of the tube 16 providing a toothbrush as disclosed in FIG. 5.

If it is desired to clean the teeth with the dental filament 36, the cover 34 is opened exposing the filament 36 as disclosed in FIG. 17. Filament 36 is accessible (FIG. 17) to be easily grasped by the user and pulled out from the spool 37 and cut off by the filament cut-off element 38. The cover, when closed, retains the extreme end of the filament 36 in the cut-off element 38 so as to conceal it completely within the housing. Subsequent use by opening cover 34 renders the filament readily available to be grasped by the user (FIG. 17).

Toothpaste is dispensed from the pouch 25 by removing the toothbrush 11 from the tube 16, opening cover 24 and then pushing the tube 16 downwardly as viewed in FIG. 3 causing the toothpaste within the pouch 25 to be dispensed out of the necks 23 and 26 (FIG. 3) onto brush 13.

When all of the toothpaste in the pouch 25 is expended, tube 16 is removed from the tube 21 and the spent pouch is replaced by a new pouch 25. The extreme end of the neck 26 of pouch 25 is snipped off either previous to the replacement or after the new pouch 25 has replaced the old pouch.

As previously stated, the dental filament dispenser 30 is a self-contained unit that can be removed from the support end 14 of the toothbrush subassembly 10.

As disclosed in FIGS. 27-33 and in accordance with my invention, the dental filament dispenser 30a can be easily and quickly attached to or detached from the tubular cover by a simple attachment means as described. In this embodiment, the toothbrush and dental filament dispenser is operated in the same way as above described in relation to FIGS. 1-7. The only difference is the attachment of the filament dispenser to the tubular cover rather than the toothbrush. In either embodiment as above described, dispensers 30 or 30a could be sold as separate units that can be carried in a pocket or container such as a lady's purse, attache case or toiletries kit.

It should also be evident from the above description that the combination of the toothbrush subassembly 10 and the dental filament dispenser 30 could be sold as a unit separate and apart from the toothpaste dispenser 20 and later the toothpaste dispenser could be added to the toothbrush subassembly 10 and dental filament dispenser 30.

Also, in an embodiment shown in FIGS. 27-33, it should be evident that both the toothbrush 11a and the dental filament dispenser 30a could be sold as separate units and used as such or combined and be used together.

It should also be evident from the above description that the present invention is constructed of a minimum number of parts, substantially all of which are capable of being molded from a plastic material. Further, the parts are easily assembled. These features make my device inexpensive to manufacture but at the same time providing maximum utility.

Although I have disclosed preferred embodiments of this invention, it should be understood that many variations can be made without departing from the spirit and scope thereof.

The embodiments of the invention in which an exclusive property or privilege is claimed are defined as follows:

1. A dental filament dispenser comprising a housing, said housing formed of a molded body having top and bottom sections, said top section having an access opening at the upper end thereof through which a spool of dental filament is received for containment in said bottom section, said access opening being defined by sides enclosing said access opening and including at least two spaced first and second sides;

a retainer for retaining said spool within said housing, said retainer separating said top and bottom sections and having an opening adjacent said second side of said access opening for receiving an end portion of the dental filament, and a cover shaped to cover said access opening and having a first edge pivotally mounted on said first side of the access opening of said housing for pivotally opening and closing said access opening and a second edge for engaging said second side of said access opening, said cover having an inside face and an exterior face; and said cover including a filament cut-off and holder element mounted on the inside face of said cover adjacent said second edge a spaced distance from the first edge, said cut-off and holder element being constructed for cutting and retaining said filament while the cover is open, said element adapted for releasably retaining the end of the filament extending from said spool after said filament is cut, said cut-off and holder element being located adjacent said second side when the cover is closed and is located above and adjacent said first side of said housing when the cover is open and thereby being spaced from said second side whereby an end portion of the filament extending through said opening in said retainer extends across said access opening when the cover is open and can be grasped while the cover is open and when the cover is closed the entire filament including said end portion is confined within said housing and when the cover is again opened, at least a portion of said filament extends from said opening in said retainer to said cut-off and holder element in spaced relationship above said access opening thereby holding and exposing said filament in a position to be grasped.

2. The dental filament dispenser of claim 1 in which said cover is molded integrally with said retainer and connected thereto with a living hinge.

3. A dental filament dispenser comprising a housing, said housing formed of a molded body having top and bottom sections, said top section having an access opening at the upper end thereof through which a spool of dental filament is received for containment in said bottom section:

a means of retaining said Spool within said housing and a cover;

said cover including a filament cut-off element mounted on said cover, said cut-off element having means for cutting said filament while the cover is open and holding the end of the filament attached to said spool whereby an end portion of the filament can be grasped while the cover is open and the entire filament including said end portion is confined within said housing when the cover is closed;

said retainer for retaining said spool including a divider member being received into said body between said upper and lower sections and closing off said access opening except for an opening therein through which said dental filament extends; and said divider member and cover being integrally molded with said body, said divider member being connected to said body with a living hinge and said cover being connected to said divider member by a living hinge.

4. A dental filament dispenser comprising a housing, said housing formed of a molded body having top and bottom sections, said top section having an access opening at the upper end thereof through which a spool of dental filament is received for containment in said bottom section;

a cover pivotally mounted on said housing for closing said access opening;

said cover including a filament cut-off and holder element mounted on the inside face of said cover at a spaced distance from the pivotal mounting of said cover on said housing whereby when the cover is opened to a position extending upwardly from said housing, said cut-off and holder element is spaced upwardly from said recess, said cut-off and holder element being constructed for cutting and retaining said filament while the cover is open, said element adapted for thereafter releasably retaining the end of the filament extending from said spool; and a retainer for holding said spool in said bottom section, said retainer having a retainer opening spaced from said pivotal mounting of said cover and receiving an end portion of the filament of said spool whereby the filament extending from said retainer opening to said cut-off and holder element and retained thereby is spaced above said access opening permitting an end portion of the filament to be grasped while the cover is open and the entire filament including said end portion is confined within said housing when the cover is closed and when the cover is again opened said filament is retained by said cut-off and holder element in an exposed position extending from said retainer opening to said cutoff and holder element on the inside surface of said open cover where said filament can be grasped.

5. The dental filament dispenser of claim 4 in which said cover is molded integrally with said retainer and connected thereto with a living hinge.

6. The dental filament dispenser of claim 4 in which said retainer and cover are integrally molded with said body, said retainer being connected to said body with a living hinge and said cover being connected to said retainer by a living hinge.

* * * * *

UNITED STATES PATENT AND TRADEMARK OFFICE
CERTIFICATE OF CORRECTION

PATENT NO. : 5,415,187
DATED : May 16, 1995
INVENTOR(S) : William R. Heneveld

It is certified that error appears in the above-indentified patent and that said Letters Patent is hereby corrected as shown below:

Column 8, line 36, claim 3;

"Spool" should be --spool--.

Signed and Sealed this

Tenth Day of October, 1995

Attest:

Attesting Officer

BRUCE LEHMAN

*Commissioner of Patents and Trademarks*